United States Patent [19]

Strutz

[11] Patent Number: 5,003,115
[45] Date of Patent: Mar. 26, 1991

[54] PRODUCTION OF 4-HYDROXYPHENETHYL ALCOHOL

[75] Inventor: Heinz Strutz, Frankfurt am Main, Fed. Rep. of Germany

[73] Assignee: Hoechst Celanese Corporation, Somerville, N.J.

[21] Appl. No.: 500,636

[22] Filed: Mar. 28, 1990

[51] Int. Cl.$^5$ .............................................. C07C 33/26
[52] U.S. Cl. .................................... 568/811; 568/715
[58] Field of Search ............... 568/811, 764, 715, 706, 568/716

[56]         References Cited
U.S. PATENT DOCUMENTS 4,760,182  7/1988  Ippolito et al.

FOREIGN PATENT DOCUMENTS 58-92406  6/1983  Japan.
558987    1/1944  United Kingdom ................ 568/764

OTHER PUBLICATIONS

Jpn. Kokai Tokkyo 63/45282, 1988, Abstract.
British UK Pat. Applic., 2187190, 1987, Abstract.
European Pat. Appl. 249245.
Japanese 86-201940 Abstract.
Tetrahedron Letters, vol. 27, No. 41, pp. 5029–5032.
LaLonde, J. Am. Chem. Soc. 98(10), 3007–13.
Hussein Naimie, Angew. Botan., 28(1), 1–43 (1964).
Shunichi Yamada, et al., Chem. Pharm. Bulletin (Tokyo) 11, 258–60 (1963).
Khafagy, et al., J. Med. Chem. (1966) 9(6), 936.
"Chemistry of Organic Compounds", Carl Noller, 1965, W. B. Saunders Company, Philadelphia, pp. 95, 195–196, 201–202.
"Organic Chemistry", Ronald F. Brown, 1975, Wadsworth Publishing Company, Belmont. Calif., pp. 367–369.
"The Condensed Chemical Dictionary", Fifth Edition, Rose, et al., 1956, Reinhold Pub. Co., N.Y., pp. 837–838.

Primary Examiner—Werren B. Lone
Attorney, Agent, or Firm—Richard S. Roberts; Shirley L. Church

[57]            ABSTRACT

A method for producing 4-hydroxyphenethyl alcohol by epoxidizing 4-acetoxystyrene with a percaboxylic acid to produce 4-acetoxyphenyl oxirane; and catalytically hydrogenating the 4-acetoxyphenyl oxirane with hydrogen to produce 4-acetoxyphenethyl alcohol; and saponifying or transesterifying the 4-acetoxyphenethyl alcohol to produce 4-hydroxyphenethyl alcohol.

17 Claims, No Drawings

PRODUCTION OF 4-HYDROXYPHENETHYL ALCOHOL

BACKGROUND OF THE INVENTION

The present invention relates to an improved process for the production of 4-hydroxyphenethyl alcohol, or more particularly to a method of producing 4-hydroxyphenethyl alcohol from 4-acetoxystyrene.

4-Hydroxyphenethyl alcohol is useful as an intermediate in the preparation of pharmaceutical compounds. It is known from U.S. Pat. No. 4,760,182 that 4-hydroxyphenethyl alcohol may be used to prepare phenoxypropanolamines, in particular the beta-adrenergic blocking agent betaxolol. It is also described in EP patent application 249 245 that it can find use as an intermediate in the preparation of the antihypertensive agents phenyl (dialkyl)dihydro- pyridinedicarboxylates. As taught in JP 86-201940 it is also useful in the preparation of (aminopropoxyphenyl) alkanols and esters which are employed in the treatment of glaucoma. From the foregoing discussion it is clear that 4-hydroxyphenyl alcohol is a well known compound and in fact, it has been produced by a variety of methods. Yamada et al, *Chem. Pharm. Bull.* (Tokyo) 11, 258–60 (1963) suggests one method of its preparation from the corresponding amine, which however is not readily accessible. Khafagy et al, *J. Med. Chem* (1966) 9 (6), 936 prepare p-hydroxyphenethyl alcohol by converting 4-hydroxyphenyl acetic acid to its ethyl ester and subsequent conversion to its acetoxy derivative. The acetoxyethyl ester is then reduced with lithium aluminum hydride and then finally saponified to give 4-hydroxyphenethyl alcohol. Hussein, *Angew. Botan.*, 38(1), 1–43 (1964) prepares p-hydroxyphenethyl alcohol in a sequence of oxidation and reduction steps from phenethyl alcohol. He additionally reports the extraction of p-hydroxyphenethyl alcohol from certain tree barks.

It has now been found that 4-hydroxyphenethyl alcohol can be prepared in yields of about 96% or more and with a high purity of about 99% or more. The process involves epoxidizing 4-acetoxystyrene, catalytically hydrogenating the resulting oxirane and saponifying or transesterifying the intermediate acetoxyphenethyl alcohol.

SUMMARY OF THE INVENTION

The invention provides a method for producing 4-hydroxyphenethyl alcohol which comprises (a) epoxidizing 4-acetoxystyrene with a percarboxylic acid to produce 4-acetoxyphenyl oxirane; and (b) catalytically hydrogenating 4-acetoxyphenyl oxirane with at least one equivalent of hydrogen per equivalent of 4-acetoxyphenyl oxirane to thereby produce 4-acetoxyphenyl alcohol; and (c) saponifying or transesterifying 4-acetoxyphenethyl alcohol to thereby produce 4-hydroxyphenethyl alcohol.

The invention also provides a method for producing 4-hydroxyphenethyl alcohol which comprises (a) catalytically hydrogenating 4-acetoxyphenyl oxirane with at least one equivalent of hydrogen per equivalent of 4-acetoxyphenyl oxirane to thereby produce 4-acetoxyphenyl alcohol; and (b) saponifying or transesterifying 4-acetoxyphenethyl alcohol to thereby produce 4-hydroxyphenethyl alcohol.

DETAILED DESCRIPTION OF THE PREFERRED EMBODIMENT

As a first step in the process of the present invention one prepares 4-acetoxyphenyl oxirane. One method of preparing 4-acetoxystyrene oxirane is disclosed in U.S. patent application Ser. No. 07/232,412, filed Aug. 15, 1988 which is incorporated herein by reference. This disclosure epoxidizes 4-acetoxystyrene with peracetic acid in which no more than a trace of mineral acid or water are present. Japanese Kokai 58-92406 (1983) discloses the preparation of p-acetoxystyrene oxirane by reacting p-acetoxystyrene with m-chloroperbenzoic acid dissolved in dichloromethane.

Hawley, *Condensed Chemical Dictionary*, (Van Nostrand Reinhold, New York, 1981) discloses the use of peracetic acid for the epoxidation of fatty acid esters and epoxy resin precursors.

Cram and Hammond, *Organic Chemistry*, (McGraw-Hill, New York, 1959), page 342, show the conversion of an alkene to an epoxide (oxirane) by oxidation with a percarboxylic acid such as peracetic acid, with the peracid being reduced to a carboxylic acid in the reaction. The authors state that carboxylic acids can open oxide rings by nucleophilic substitution reactions. Acetoxystyrene oxirane has the formula

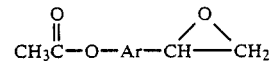

where Ar is a 1,4-phenylene group with the 1-carbon bonded to the epoxide (oxirane) group and the 4-carbon bonded to the acetoxy group, and wherein the ring carbon atoms are bonded to hydrogen atoms. The epoxidation of the 4-ace-toxystyrene proceeds with a percarboxylic acid such as m-chloroperbenzoic acid or more preferably peracetic acid according to the reaction

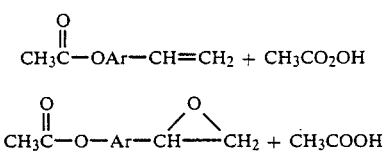

In carrying out the foregoing reaction, a solution of about 30 to 40 wt % of peracetic acid in acetic acid containing no more than a trace of mineral acid and water and preferably mixed with an organic solvent, is contacted with the 4-acetoxystyrene, preferably mixed with the same organic solvent as the peracetic acid/acetic acid mixture.

The epoxidation reaction is carried out at a temperature of about 0° C. to about 25° C., for example, about 2 to 48 hours. After the reaction is complete, the reaction mixture is desirably washed with water and an aqueous solution of a mild base, e.g., sodium bicarbonate, dried over an insoluble dehydrating agent, e.g., magnesium sulfate or sodium sulfate, and concentrated under vacuum to obtain the 4-acetoxystyrene oxirane product.

The 4-acetoxystyrene oxirane is then catalytically hydrogenated with at least one equivalent of hydrogen per equivalent of 4-acetoxystyrene oxirane to produce 4-acetoxyphenethyl alcohol. This may be formed by dissolving 4-acetoxystyrene with a suitable solvent, and charging the mixture into an autoclave with a suitable catalyst. The autoclave is purged with nitrogen and then pressurized with an excess of hydrogen gas until the conversion to 4-acetoxyphenethyl alcohol is essentially complete.

Suitable solvents non-exclusively include ethanol, methanol, isopropanol and acetic acid. Non-exclusive examples of catalysts include, Pd/C, Pt/C, Ru/C, Pt/Al$_2$O$_3$, copper chromite and Raney Nickel. In the preferred embodiment, the catalyst is present in an amount of from about 0.01% to about 400%, or more preferably from about 0.1% to about 250%, and most preferably from about 1.0% to about 200%, based on the weight of 4-acetoxystyrene.

In the preferred embodiment, the hydrogenation is conducted at a pressure of from about 15 psig to about 2,000 psig, or more preferably from about 15 psig to about 1,000 psig, and most preferably from about 15 psig to about 400 psig.

In the preferred embodiment, the hydrogenation step is conducted for from about 3 minutes to about 240 minutes, or more preferably from about 6 minutes to about 120 minutes, and most preferably from about 10 minutes to about 60 minutes.

In the preferred embodiment the hydrogenation is conducted at a temperature of from about 0° C. to about 100° C. or more preferably from about 15° C. to about 45° C.

The next step in the overall process is the saponification or transesterification of 4-acetoxyphenethyl alcohol to 4-hydroxyphenethyl alcohol. The saponification may basically be conducted by dissolving the 4-acetoxyphenethyl alcohol in a compatible solvent and reacting with a hydroxide or acid. Suitable solvents non-exclusively include methanol, ethanol and water. If an alcohol is used in the hydrogenation step, this solvent is preferably used in the saponification step or in the transesterification. The solvent is present in an amount sufficient to dissolve the composition components. Suitable hydroxides include alkali metal, alkaline earth metal and ammonium hydroxide. In the preferred embodiment, the hydroxide is used in a molar excess, i.e., from about 1.0 mol to about 10 mols, or more preferably from about 1.5 mols to about 8 mols, and most preferably from about 2.0 mols to about 5 mols of hydroxide per mole of 4-acetoxyphenethyl alcohol.

The transesterification is acid catalyzed and a few drops of an acid such as sulfuric acid may be used for this purpose.

In the preferred embodiment, the saponification or transesterification step is conducted for from about 10 minutes to about 600 minutes, or more preferably from about 20 minutes to about 300 minutes, and most preferably from about 30 minutes to about 180 minutes. The saponification or transesterification is best performed at the boiling point of the solvent.

The following non-limiting examples serve to illustrate the invention.

EXAMPLE 1

4-Acetoxystyrene oxide

Commercially available peracetic acid (57 g) produced by the oxidation of acetic acid with hydrogen peroxide using sulfuric acid as catalyst, and containing about 35 wt % of peracetic acid, about 19 wt % of water, about 0.6 wt % of hydrogen peroxide, about 1 wt % of sulfuric acid, and the remainder acetic acid, is mixed with chloroform (250 ml) and transferred to a separatory funnel. The upper aqueous layer is discarded and the chloroform layer is dried over magnesium sulfate and filtered to yield a solution containing about 37 wt % of peracetic acid, about 0.6% wt of hydrogen peroxide, and the remainder acetic acid. No more than a trace of sulfuric acid or water is detectable. The solution is added dropwise to an ice cold solution of 4-acetoxystyrene (24.3 g, 0.15 mol) in chloroform (150 ml) containing sodium acetate (5.0 g). After the addition of peracetic acid solution, the reaction mixture is warmed up to room temperature and stirred overnight. The reaction mixture is washed with water (3×200 ml) and saturated sodium bicarbonate solution (3×200 ml), dried over anhydrous magnesium sulfate, filtered, and concentrated in-vacuo to afford an oil characterized by NMR analysis as 4-acetoxystyrene oxide (26.2 g, 98% yield).

EXAMPLE 2

4-Acetoxyphenethyl alcohol

A 300 ml Fluitron autoclave (Hastelloy C) is charged with 69.5 g crude acetoxystyrene oxirane (86%; 0.335 mol), 200 ml ethanol and 1.6 g Pd/C (5% Pd on carbon; 47.8% H$_2$O). After sealing, the stirrer is started, and the autoclave purged with nitrogen and hydrogen and then pressurized to 400 psig with hydrogen. The H$_2$ pressure is kept constant during the one hour reaction period. The autoclave is vented and purged with N$_2$. The reaction mixture is sucked out of the reactor (63.2 g ethanol rinse) and filtered (23.7 g ethanol rinse).

Saponification of the hydrogenation product 4-acetoxyphenethyl alcohol

In a 500 ml flask equipped with stirrer and reflux condenser, the filtered reaction mixture (total: 300.6 g) is mixed with 34.7 g KOH (0.62 mol) and 11.6 g water and refluxed for 3 hrs. The amber solution is cooled to room temperature and adjusted to pH 6 by adding concentrated HCl. KCl is removed by filtration (20.2 g ethanol rinse), and the filtrate further clarified by adding 36.4 g water (total: 389.5 g). This mixture is analyzed for 4-hydroxyphenethyl alcohol by GC: 11.4 wt. %=44.4 g (0.32 mol=95.9 mol-% with respect to 4-acetoxystyrene oxirane.

Refining procedure for crude 4-hydroxyphenethyl alcohol:

988 g of the above saponified hydrogenation product corresponding to about 100 g 4-hydroxyphenethyl alcohol is freed of most of the ethanol, diluted with 150 ml water and then extracted four times with 250 ml ethyl acetate respectively. After drying over MgSO$_4$, ethyl acetate is stripped off in vacuo (70° C., 120 mmHg, then 0.25 mmHg at room temperature) to yield a tan solid (123.1 g).

The tan product is dissolved in about 640 g ethyl acetate, treated with 0.1 NaBH$_4$ and 2.5 g carbon and filtered over Celite (119 g ethyl acetate rinse). The filtrate, which still has the same color as the original solution, is mixed with 280 g toluene. By the dropwise addition of 670 g hexane, a dark brown oil separates out from which the orange brown solution is decanted. Another 1630 g hexane are necessary to precipitate 86.9 of a light brown product; from the mother liquor an additional 4.1 g product can be isolated.

Purity by GC: 98.2%

Recovery: >89% (based on content in the crude mixture)

A simple distillation (no column) at 145° C./0.5 mmHg provides an almost white material (after pulverization)

Purity by GC: >99%
Recovery: 83% (based on recrystallized product)
m.p.: 91° C.

EXAMPLE 3

Example 2 is repeated except using 6 g of crude acetoxystyrene oxirane (84.0–86.2%) in 80 ml ethanol at room temperature for 1 hour. Table 1 lists changed reaction conditions and results.

TABLE 1

| Catalyst | Catalyst Weighed g | Hydrogen Pressure PSIG | Yield[1] MOL % |
|---|---|---|---|
| Pd/C(5%) | 0.1 | 15 | 92.4 |
| Pd/C(5%) | 10.0 | 400 | 100.8 |
| Pd/C(5%) | 5.0 | 200 | 99.8 |
| Pd/C(5%) | 10.0 | 15 | 95.9 |
| Pd/C(5%) | 0.1 | 400 | 99.2 |
| Pt/C(5%) | 0.6 | 400 | 52.5 |
| Ru/C(5%)[2] | 0.6 | 400 | 21.4 |
| Pt/A2O3(5%) | 0.6 | 400 | 56.3 |
| Cu chromite[2,3] | 0.6 | 400 | 8.0 |
| Ra-Ni | 0.3[4] | 15 | 19.5 |
| Ra-Ni | 2.8[4] | 400 | 79.7 |
| Ra-Ni/NaOH | 2.8[4]/0.32 | 15 | 68.8 |
| Pd/C(5%) | 5.0 | 200 | 105.7 |
| Pd/C(5%) | 10.0 | 400 | 103.7 |

1. Yield of 4-hydroxyphenethyl alcohol with respect to acetoxystyrene oxirane content after saponification of the hydrogenation product. GC analysis accuracy +/−5%. Figures over 100% are due to experimental or analytical error.
2. 70° C.
3. Calsicat 96C-050 from Mallinckrodt
4. Wet

EXAMPLE 4

Example 3 is repeated except using 200 ml ethanol and Pd/C (5%) catalyst, 400 psig $H_2$, at room temperature for 1 hour. Table II lists the results under these reaction condition.

TABLE II

| Weight of Crude acetoxystyrene oxirane (g) | Weight % of acetoxystyrene oxirane | Weight Pd/C (5%) (g) | Yield* mol % |
|---|---|---|---|
| 45.0 | 75 | 1 | 97.3 |

*Yield of 4-hydroxyphenethyl alcohol as determined by GC of the reaction mixture after saponification.

What is claimed is:

1. A method for producing 4-hydroxyphenethyl alcohol which comprises
   (a) epoxidizing 4-acetoxystyrene with a percarboxylic acid to produce 4-acetoxyphenyl oxirane; and
   (b) catalytically hydrogenating 4-acetoxyphenyl oxirane with at least one equivalent of hydrogen per equivalent of 4-acetoxyphenyl oxirane to thereby produce 4-acetoxyphenethyl alcohol; and
   (c) saponifying or transesterifying 4-acetoxyphenethyl alcohol to thereby produce 4-hydroxyphenethyl alcohol.

2. The method of claim 1 wherein step (a) is conducted with peracetic acid or meta-chloroperbenzoic acid.

3. The method of claim 1 wherein step (b) is conducted with a catalyst selected from the group consisting of Pd/C, Pt/C, Ru/C, Pt/Al2O3, copper chromite and Raney Nickel.

4. The method of claim 1 wherein step (b) is conducted at a pressure of from about 15 to about 400 PSIG.

5. The method of claim 1 wherein step (b) is conducted at a temperature of from about 0° C. to about 100° C.

6. The method of claim 1 wherein step (c) is conducted with an alkali metal, alkaline earth metal or ammonium hydroxide.

7. The method of claim 1 wherein step (c) is conducted under strongly acidic conditions.

8. The method of claim 7 wherein step (c) is conducted with sulfuric acid or methane sulfonic acid.

9. A method for producing 4-hydroxyphenethyl alcohol which comprises
   (a) catalytically hydrogenating 4-acetoxyphenyl oxirane with at least one equivalent of hydrogen per equivalent of 4-acetoxyphenyl oxirane to thereby produce 4-acetoxyphenethyl alcohol; and
   (b) saponifying or transesterifying 4-acetoxyphenethyl alcohol to thereby produce 4-hydroxyphenethyl alcohol.

10. The method of claim 9 wherein step (a) is conducted with a catalyst selected from the group consisting of Pd/C, Pt/C, Ru/C, Pt/Al2O3, copper chromite and Raney Nickel.

11. The method of claim 9 wherein step (a) is conducted at a pressure of from about 15 to about 400 PSIG.

12. The method of claim 9 wherein step (a) is conducted at a temperature of from about 0° C. to about 100° C.

13. The method of claim 9 wherein step (b) is conducted with an alkali metal, alkaline earth metal or ammonium hydroxide.

14. The method of claim 9 wherein step (b) is conducted under strongly acidic conditions.

15. The method of claim 14 wherein step (b) is conducted with sulfuric acid or methane sulfonic acid.

16. The method of claim 1 wherein step (a) is conducted with peracetic acid or meta-chlorobenzoic acid; step (b) is conducted with a catalyst selected from the group consisting of Pd/C, Pt/C, Ru/C, Pt/Al2O3, copper chromite and Raney Nickel, and step (b) is conducted at a pressure of from about 15 to about 400 PSIG at a temperature of from about 0° C. to about 100° C.; and wherein step (c) is conducted with a component selected from the group consisting of an alkali metal hydroxide, an alkaline earth metal hydroxide, ammonium hydroxide, sulfuric acid or methane sulfonic acid.

17. The method of claim 9 wherein step (a) is conducted with a catalyst selected from the group consisting of Pd/C, Pt/C, Ru/C, Pt/Al2O3, copper chromite and Raney Nickel, and step (b) is conducted at a pressure of from about 15 to about 400 PSIG at a temperature of from about 0° C. to about 100° C.; and wherein step (b) is conducted with a component selected from the group consisting of an alkali metal hydroxide, an alkaline earth metal hydroxide, ammonium hydroxide, sulfuric acid or methane sulfonic acid.

* * * * *